United States Patent
Buchecker et al.

(10) Patent No.: US 6,676,851 B1
(45) Date of Patent: Jan. 13, 2004

(54) LATERALLY SUBSTITUTED CURABLE LIQUID CRYSTALS

(75) Inventors: Richard Buchecker, Zurich (CH); Teodor Lukac, Basel (CH); Carsten Benecke, Weil Am Rhein (DE)

(73) Assignee: Rolic AG, Zug (CH)

(*) Notice: Subject to any disclaimer, the term of this patent is extended or adjusted under 35 U.S.C. 154(b) by 0 days.

(21) Appl. No.: 09/913,598

(22) PCT Filed: Feb. 1, 2000

(86) PCT No.: PCT/IB00/00098

§ 371 (c)(1),
(2), (4) Date: Aug. 16, 2001

(87) PCT Pub. No.: WO00/48985

PCT Pub. Date: Aug. 24, 2000

(30) Foreign Application Priority Data

Feb. 17, 1999 (GB) .............................................. 9903670

(51) Int. Cl.$^7$ .............................................. C09K 19/20
(52) U.S. Cl. ............................ 252/299.67; 252/299.61; 252/299.63; 560/61; 560/85; 428/1
(58) Field of Search ....................... 252/299.67, 299.01, 252/299.61, 299.63; 560/61, 85

(56) References Cited

U.S. PATENT DOCUMENTS 5,164,111 A * 11/1992 Dorsch et al. .......... 252/299.01
5,593,617 A * 1/1997 Kelly et al. ............ 252/299.67
6,319,963 B1 * 11/2001 Coates et al. ................ 428/1.1

FOREIGN PATENT DOCUMENTS

| WO | WO 99 37735 A | 7/1999 |
| WO | WO 99 64924 A | 12/1999 |
| WO | WO 00 04110 A | 1/2000 |

* cited by examiner

Primary Examiner—Mark F. Huff
Assistant Examiner—Jennifer R. Sadula
(74) Attorney, Agent, or Firm—Finnegan, Henderson, Farabow, Garrett, & Dunner, L.L.P.

(57) ABSTRACT

In one embodiment, the invention relates to compounds of the formula (I)

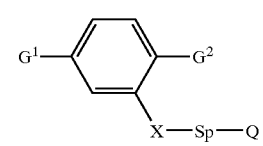

wherein G1 and G2 independently represent a polymerizable mesogenic residue, and X, Sp, and Q are as defined herein. The compounds of the invention may, for example, be useful as curable liquid crystals and for preparing liquid crystal films.

16 Claims, No Drawings

LATERALLY SUBSTITUTED CURABLE LIQUID CRYSTALS

This application is a national stage filing of International Application No. PCT/IB00/00098, filed Feb. 1, 2000, which published in the English language. This application also claims the benefit of priority under 35 U.S.C. § 119(a) to GB Application No. 9903670.9, filed on Feb. 17, 1999.

The present invention relates to laterally substituted curable Liquid Crystals (LCPs) having mesogenic properties or properties which cause these LCPs to be compatible with a mesogenic molecular architecture. In particular the present invention relates to laterally substituted curable Liquid Crystals (LCPs) having a low melting point and good alignment properties and the use of such LCPs in the preparation of substantially uniform or patterned films in which the orientation of the LCP molecules in the plane and relative to the plane of the substrate can be controlled.

Films prepared from curable Liquid Crystals (LCP films) are well known to a skilled person and are used in the preparation of optical and electro-optical devices. These films are generally manufactured by using coating techniques such as spin coating. This involves casting an organic solution of a cross-linkable LCP or LCP mixture onto a substrate provided with an orientation layer. The organic solvent is subsequently removed to give a well orientated, solvent free mesogenic LCP layer. This mesogenic LCP layer may be cross-linked to give a LCP film. The thickness of the LCP film depends upon the viscosity and therefore the concentration of the organic solution of the polymerisable LCP mixture used in the coating process. The uniformity of the film formed depends upon the ability of the LCPs to form homogeneous layers free of tilt domains as well as the stability of the LCP mixture during the coating and cross-linking processes. By the term "tilt domains" it should be understood to mean regions within the LCP film in which the long axis of the LCP molecules form tilt angles with the substrate plane which are of the same size, but have opposite directions.

A problem with known LCPs, especially those having high clearing and melting points, is that they are not able to form mixtures that remain stable during both the coating and cross-linking processes. These prior art LCP mixtures tend to be characterised by a poor solubility in organic solvents; a tendency for the components of the mixture to separate from one another; and a tendency to crystallise. Although attempts have been made to solve these problems by, for example, preparing LCPs with lower melting points, the ability of these prior art LCPs to align with the tilt direction imposed on the film tends to be poor. Such poorly aligned films tend to be characterised by a low contrast ratio.

A further problem associated with existing LCP materials is the formation of tilt domains and disclinations during the preparation of LCP films. By the term disclination it should be understood to mean borderlines of neighbouring tilt domains where LCP molecules of opposite tilt angles are adjacent. These tilt domains and disclinations result in both a disturbance in the uniform appearance of the film and an inhomogeneous optical performance.

The aforementioned problems are of particular relevance if photooriented and photopatterned orientation layers are used for the orientation of LCPs. This so called linear photopolymerisation (LPP) technology (*Nature,* 381, p. 212 (1996) allows the production of not only uniform but also structured (photopatterned) orientation layers. If such structured orientation layers are used for the orientation of LCPs, the LCP molecules should adapt the information given by the orientation layer with respect to the direction of alignment and the tilt angle in each single pixel individually.

There is, therefore, a need for a new LCP material that may be used in the preparation of LCP mixtures and layers, which significantly reduces the aforementioned disadvantages and which is especially suitable when applied to LPP orientation layers. The present invention addresses that need.

A first aspect of the invention provides a compound of formula (I)

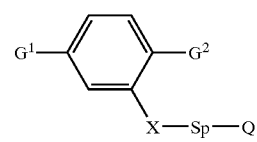

wherein
$G^1$ and $G^2$ independently represent a polymerisable mesogenic residue;

X represents a group selected from —CH$_2$—, —O—, —CO—, —COO—, —OOC—, —CONR'—, —OCOO—, —OCONR';

Sp represents a group of the formula —(CH$_2$)p— in which p is an integer of 1 to 18 and in which one or two non adjacent —CH$_2$— groups are optionally replaced by —CH=CH—; or in which one or two —CH$_2$— groups are optionally replaced by one or two groups selected from the group consisting —O—, —CO—, —COO—, —OOC—, —CONR'—, —OCOO—, —OCONR'— with the proviso that firstly the spacer group does not contain two adjacent heteroatoms and secondly when X is —CH$_2$—, p can also have a value of 0;

Q represents a a polar group selected from —CN, —COR, —COOR, —OCOR, —CONR'R, —NR'COR, —OCOOR, —OCONR'R, —NR'COOR, F, Cl, —CF$_3$, —OCF$_3$ or —OR or a cyclic group which is unsubstituted or optionally substituted by a group selected from a lower alkyl, lower alkenyl, lower alkoxy, lower alkenyloxy, halogen, —CN, —COR", —COOR", —OCOR", —CONR'R", —NR'COR", —OCOOR", —OCONR'R", —NR'COOR", —CF$_3$, and —OCF$_3$;
where
R represents hydrogen, a lower alkyl, a lower alkenyl or a cyclic group as defined above; and
R' is hydrogen, a lower alkyl or a lower alkenyl group
R" represents a lower alkyl or a lower alkenyl group.

The compounds of the invention have been found to have lower melting points compared to the compounds of the prior art. They have also been found to be more miscible with other components of the liquid crystal mixtures of which they form a part. have a reduced tendency to crystallise from and little effect on the clearing points of such mixtures. In addition they exhibit improved alignment abilities compared to the compounds of the prior art.

Laterally substituted mesogenic compounds are known from WO 95/24454, WO 95/24455, U.S. Pat. Nos. 5,650, 534, 5,593,617, 5,567,347 and 5,707,544. However, many of these compounds are not suitable for preparing LCP films and networks that are substantially free of tilt domains. Others exhibit high melting points, higher viscosities (U.S. Pat. No. 5,567,347), lower clearing points (U.S. Pat. No. 5,593,617), poor solubility and/or poor orientation properties. It has been found that by using the compounds of the present invention it is possible to control the orientation or alignment of LCPs or LCP mixtures in the plane of the substrate, to form a tilt angle relative to the plane and to suppress the formation of tilt domains in the mesogenic layers and films formed. The compounds of the invention may therefore be used in the preparation of high contrast optical or electro-optical devices.

The compounds of the invention have also been found to be highly miscible with other LCP compounds over a broad range of concentrations. These compounds and mixtures containing them are extremely soluble in organic solvents. These properties mean that it is possible to prepare coating solutions having a concentration and viscosity that can be controlled over a wide range. Consequently, the thickness of the LCP layers formed using these coating solutions can be readily controlled.

The compounds of the invention are further characterised by relatively low melting points and clearing points that are generally above room temperature. Therefore, during the formation of LCP films or networks using the compounds of the invention or mixtures thereof, spontaneous crystallisation does not tend to occur. This property (otherwise known as supercooling) greatly facilitates the formation of LCP films and networks free of defects. This further means that it is also possible to reduce the number of liquid crystal components used in the manufacture of LCP mixture.

The polymerisable mesogenic residues $G^1$ and $G^2$ may be the same or different, but are preferably the same.

The group X is preferably selected from —$CH_2$—, —O—, —COO— and —OOC—.

The spacer group Sp may be optionally substituted by one or more fluorine atoms. Groups in which there are no substituent groups present are preferred. It is especially preferred that the integer p has a value of from 1 to 11 and that no more than one —$CH_2$— group is replaced by —CH=CH—, —O—, CO—, —COO—, —OOC—, —CONR'—, —OCOO—, —OCONR'.

The group Q is preferably selected from —CN, —COOR, —OCOR, Cl, —$CF_3$, —$OCF_3$ and —OR in which R is defined as above. The cyclic group may be a saturated or unsaturated, isocyclic or heterocyclic five or six membered cyclic group. The cyclic group may be unsubstituted or may contain one or two substituents independently selected from the group consisting a lower alkyl, lower alkenyl, lower alkoxy, lower alkenyloxy, halogen, —CN, —COR", —COOR", —OCOR", —CONR'R", —NR'COR", —OCOOR", —OCONR'R", —NR'COOR", —$CF_3$, —$OCF_3$ and —OR" in which R' is as defined above and R" represents a lower alkyl or a lower alkenyl group. Preferred halogen substituents for the cyclic group include F and Cl.

Preferred five membered cyclic groups included in the group Q are selected from the group consisting of optionally substituted furanyl, tetrahydrofuranyl, dioxolanyl, oxazolyl, 3,4-dihydrooxazolyl and cyclopentyl. Especially preferred five membered cyclic groups include 2-furanyl, 2-tetrahydrofuranyl, 2-dioxolanyl and 3,4-dihydo-2-oxazolyl.

Preferred six membered cyclic groups included in the group Q are selected from the group consisting of an optionally substituted phenyl, pyridinyl, pyrimidinyl, cyclohexyl, cyclohexenyl, tetrahydropyranyl, 1,3-dioxanyl. Especially preferred six membered groups include phenyl, cyclohexyl, 1,3-dioxan-2-yl and 2-tetrahydropyranyl.

It is preferred that the five or six membered cyclic groups are unsubstituted or contain no more than one substituent group. If a substituent group is present, it is preferably selected from the group consisting of a lower alkyl, lower alkoxy, F, Cl, —CN, —COOR", —OCOR", —$OCF_3$, OR", in which R" is lower alkyl.

By the term "lower alkyl" it should be understood to include a $C_{1-6}$ achiral, branched or straight-chained alkyl group. Examples of lower alkyl groups that may be present in the compounds of the invention include methyl, ethyl, propyl, butyl, pentyl hexyl and the like.

By the term "lower alkenyl" it should be understood to include $C_{3-6}$ achiral, branched or straight-chained alkenyl group in which the double bond is at position 2- or higher. Examples of lower alkenyl groups that may be present in the compounds of the invention include 2-propylene, 3-butylene, 3-isopentylene, 4-pentylene and the like.

By the term "lower alkoxy" it should be understood to include $C_{1-6}$ achiral, branched or straight-chained alkoxy group. Examples of lower alkoxy groups that may be present in the compounds of the invention include methoxy, ethoxy, propoxy, butoxy, pentoxy, hexoxy and the like.

Preferably the polymerisable mesogenic residues $G^1$ and $G^2$ are each independently represented by the group of formula II

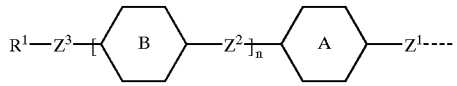

II wherein
A and B are independently selected from the group consisting of 1,4-phenylene, pyridine-2,5-diyl, pyrimidine-2,5-diyl, trans-1,4-cyclohexylene and trans-1,3-dioxane-1,4-diyl; optionally substituted with a halogen, —CN, a lower alkyl, lower alkenyl, lower alkoxy or lower alkenyloxy group;

n is 1 or 0, $Z^1$ and $Z^2$ are independently selected from the group consisting a single bond, —COO—, —OOC—, —$CH_2$—$CH_2$—, —$CH_2O$—, —$OCH_2$—, —CH=CH—, —C≡C—, —$(CH_2)_4$—, or —$(CH_2)_3O$—;

$Z^3$ represents a group of formula —$(CH_2)_pX$— in which p is an integer having a value of 1 to 18 and X is defined above, and in which one or two non adjacent —$CH_2$— groups may be optionally replaced by —CH=CH— or in which one or two —$CH_2$— groups may be replaced by one or two additional linking groups X with the proviso that firstly the group $Z^3$ does not contain two adjacent heteroatoms and secondly when X is —$CH_2$, p can also have a value of 0

$R^1$ represents a polymerisable group selected from the group consisting of $CH_2$=C(Ph)—, $CH_2$=CW—COO—, $CH_2$=CH—COO—Ph-, $CH_2$=CW—CO—NH—, $CH_2$=CH—O—, $CH_2$=CH—OOC-, Ph-CH=CH—, $CH_2$=CH-Ph-, CH=CH-Ph-O—, $R^3$-Ph-CH=CH—COO—, $R^3$—OOC—CH=CH-Ph-O— and 2-W-epoxyethyl in which W represents H, Cl, Ph or a lower alkyl, $R^3$ represents a lower alkyl with the proviso that when $R^3$ is attached to a phenylene group (-Ph-) it may also represent hydrogen or a lower alkoxy.

The terms "Ph" and "Ph-" will be understood to indicate a phenyl group, and "-Ph-" any isomer of phenylene, namely 1,2-phenylene, 1,3-phenylene or 1,4-phenylene, except where the context requires otherwise.

The groups A and B may be optionally substituted with a halogen, —CN, a lower alkyl, lower alkenyl, lower alkoxy or lower alkenyloxy group. If a halogen substituent is present this is preferably F or Cl. It is preferred that the groups A and B are selected from optionally substituted 1,4-phenylene and 1,4-cyclohexylene rings. It is especially preferred that the groups A and B are unsubstituted.

By the term "alkenyloxy" it should be understood to include $C_{3-6}$ achiral, branched or straight-chained alkenyloxy group in which the double bond is at position 2- or higher. Examples of lower alkenyloxy groups that may be present in the compounds of the invention include 2-propenyloxy, 3-butenyloxy, 4-pentenyloxy, 5-hexenyloxy and the like.

It is preferred that the groups $Z^1$ and $Z^2$ are selected from the group consisting a single bond, —COO—, —OOC—, —$CH_2$—$CH_2$—, —$CH_2O$—, —$OCH_2$—, —CH=CH— and —C≡C—. It is especially preferred that $Z^1$ and $Z^2$ represent a single bond, —C≡C—, —COO— or —OOC—.

$Z^3$ may be optionally substituted by one or more halogen atoms, preferably one or more fluorine atoms. It is preferred that p has a value of 1 to 11. It is also preferred that $Z^3$ contains no substitution. It is further preferred that, for the group $Z^3$, X is selected from —$CH_2$—, —O—, —COO— and —OOC—, especially —$CH_2$—or —O—.

It is preferred that the group $R^1$ is selected from the group consisting $CH_2$=CW—, $CH_2$=CW—COO— and $CH_2$=CH—O—.

It is preferred that the sum of the two integers n for each of the groups $G^1$ and $G^2$ is 0 or 1. It is especially preferred that for both $G^1$ and $G^2$ n has a value of 0.

The compounds of the invention may be readily prepared using procedures well known to a skilled person accordance with any one of the procedures set out in Schemes 1 to 6 below.

Scheme 1
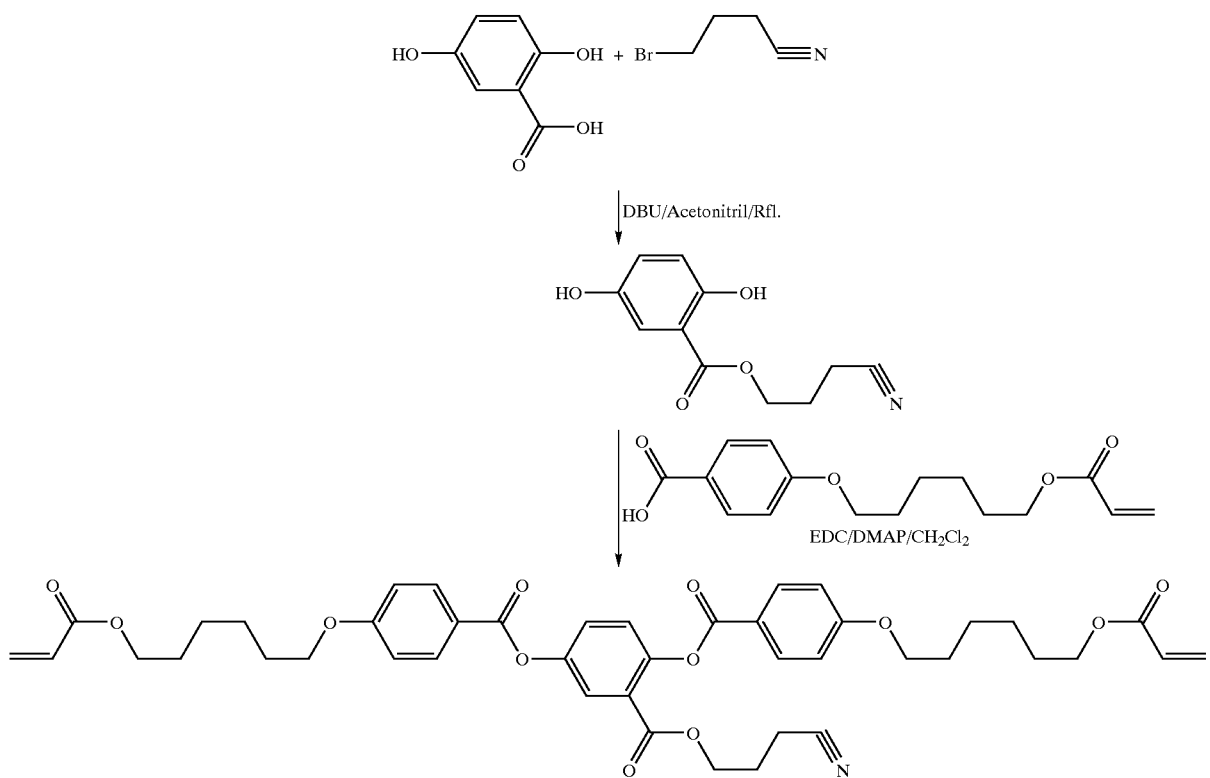
in which:
DBU is 1,8-diazabicyclo[5.4.0]undec7-ene
EDC is N(3-dimethylaminopropyl)-N'-ethylcarbodiimide hydrochloride
DMAP is 4-dimethylaminopyridine
Scheme 2
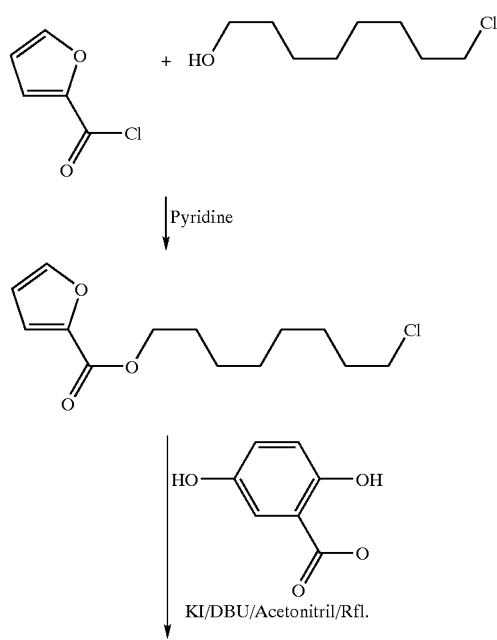

-continued
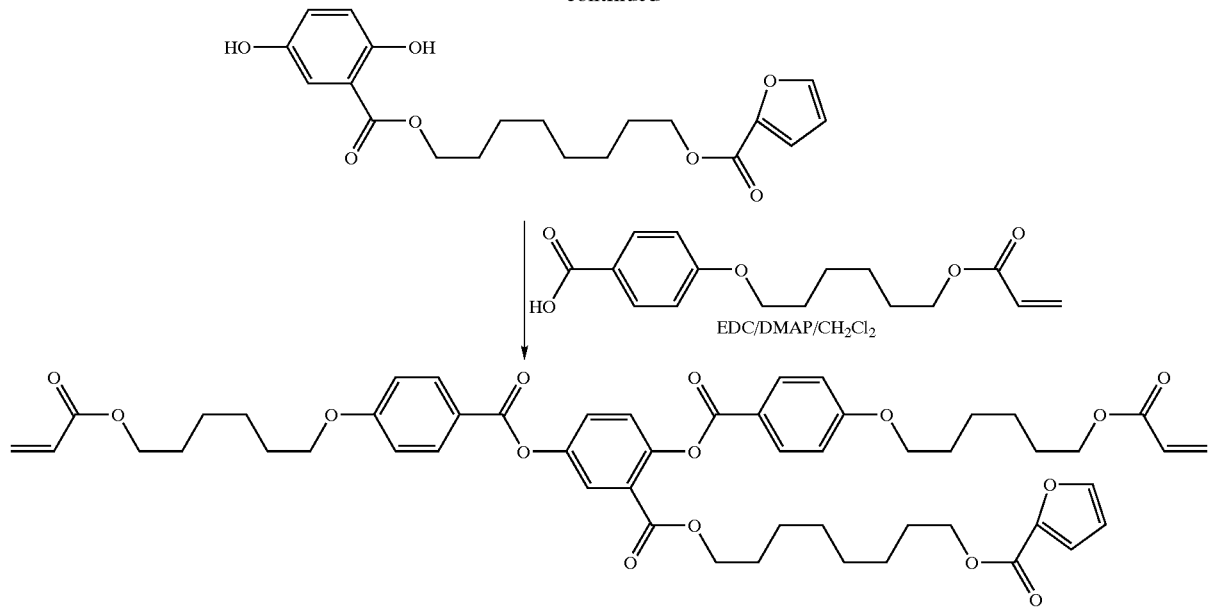
in which:
 DBU is 1,8-diazabicyclo[5.4.0]undec-7-ene
 KI is potassium iodide
EDC is N-(3-dimethylaminopropyl)-N'-ethylcarbodiimide hydrochloride
DMAP is 4-dimethylaminopyridine
Scheme 3
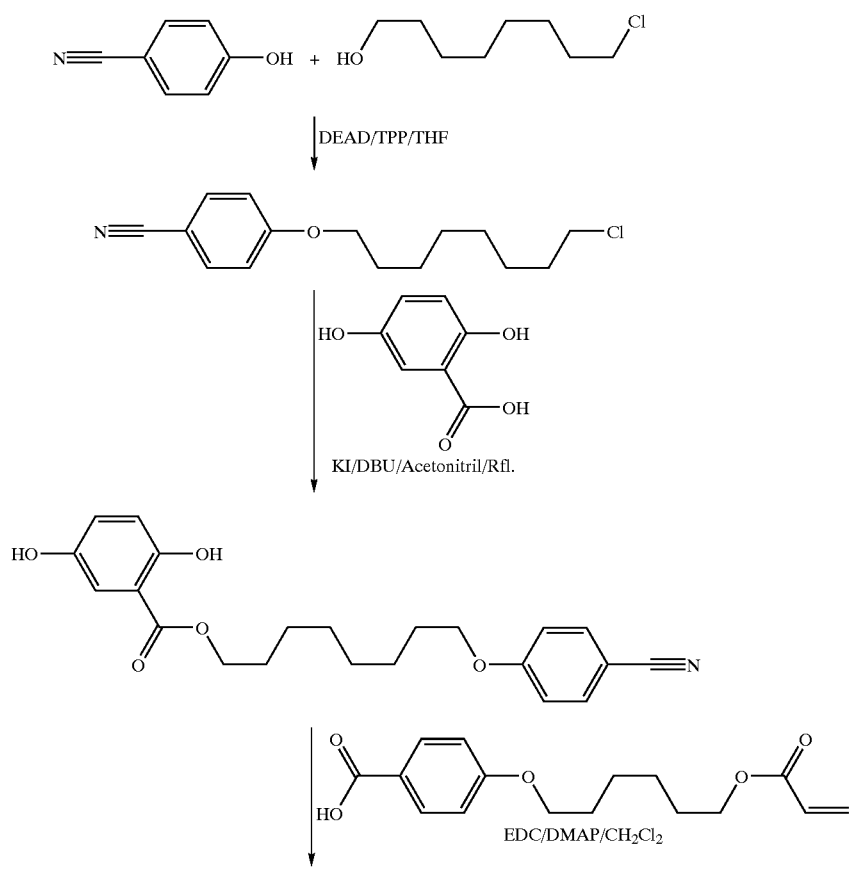

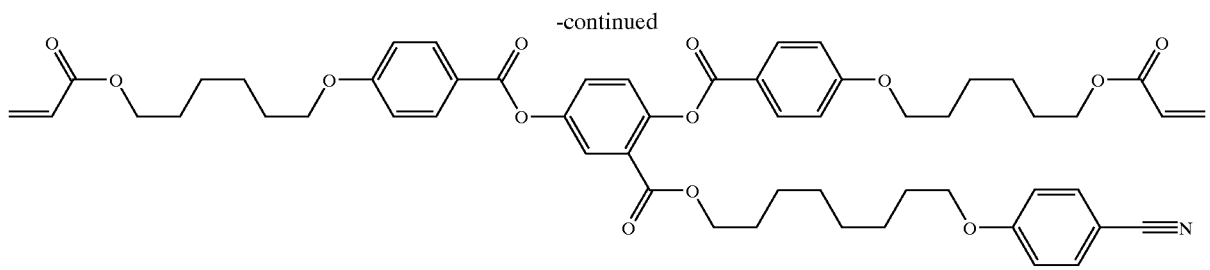
in which:
DEAD is diethyl azodicarboxylate
KI is potassium iodide
DBU is 1,8-diazabicyclo[5.4.0]undec-7-ene
EDC is N-(3-dimethylaminopropyl)-N'-ethylcarbodiimide hydrochloride
DMAP is 4-dimethylaminopyridine
Scheme 4
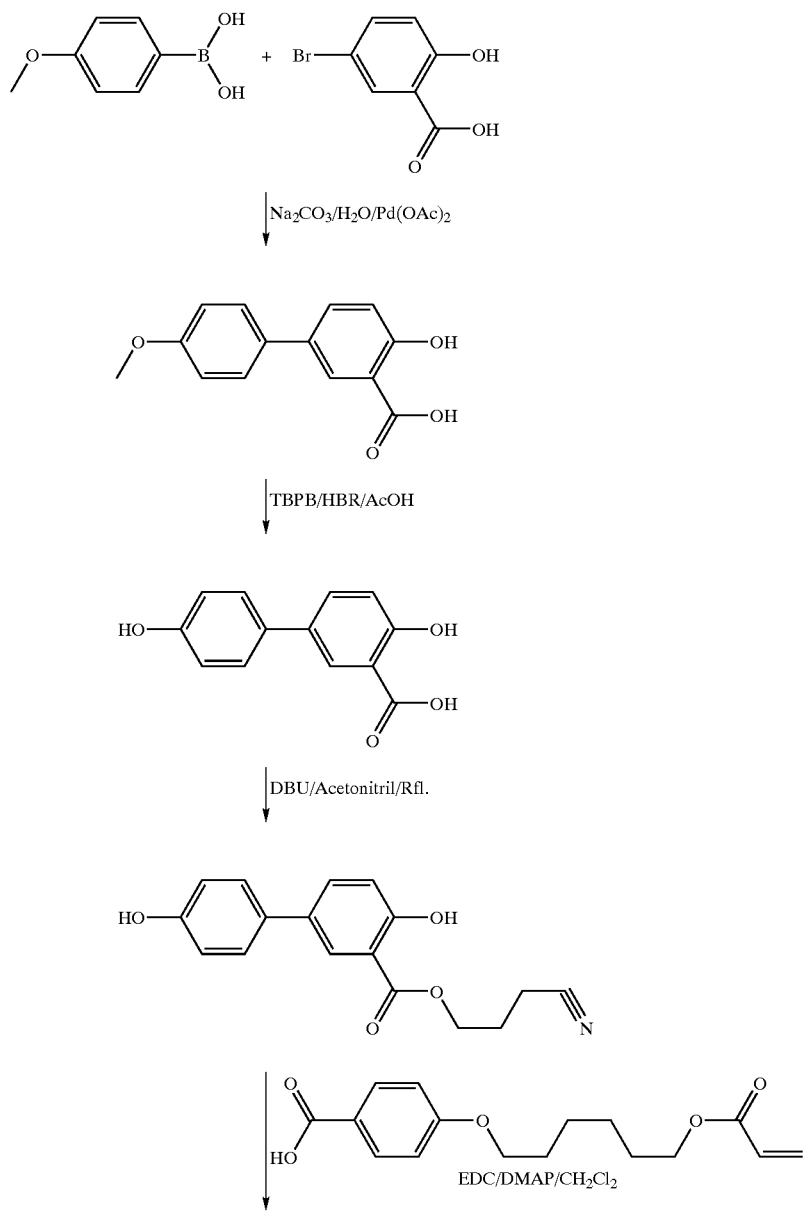

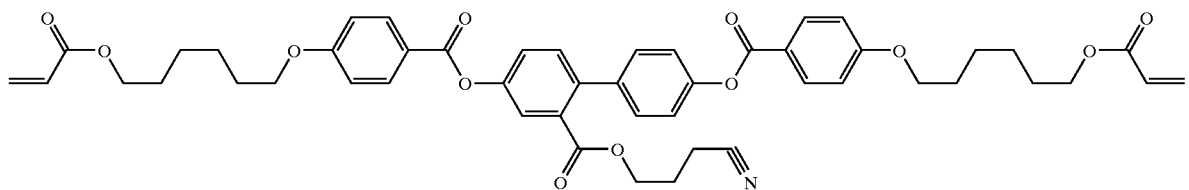
in which:
TBPB is tetrabutylphosphonium bromide
HBr is 48-% hydrobromic acid
AcOH is acetic acid
DBU is 1,8-diazabicyclo[5.4.0]undec-7-ene
EDC is N-(3-dimethylaminopropyl)-N'-ethylcarbodiimide hydrochloride
DMAP is 4-dimethylaminopyridine
Scheme 5
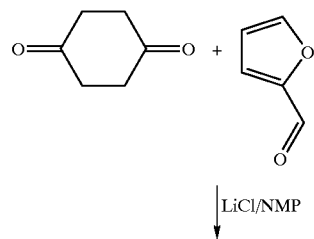
↓ LiCl/NMP
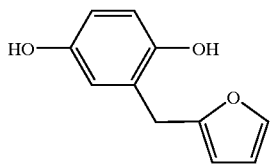
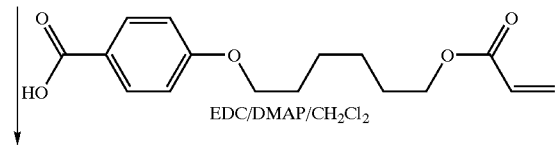
EDC/DMAP/CH$_2$Cl$_2$
↓
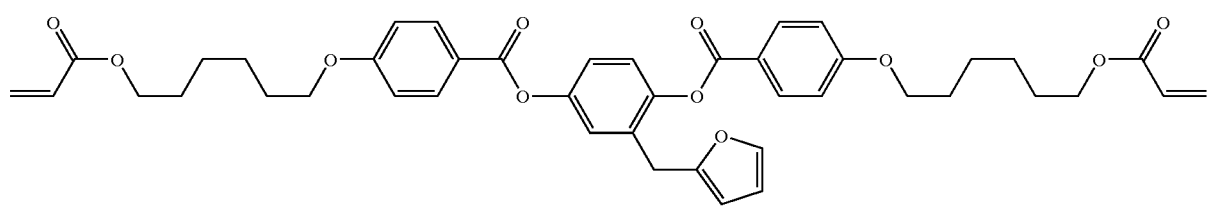

in which:

NMP is 1,3-dimethyl-2-imidazolidinone

EDC is N-(3-dimethylaminopropyl)-N'-ethylcarbodiimide hydrochloride

DMAP is 4-dimethylaminopyridine

Scheme 6

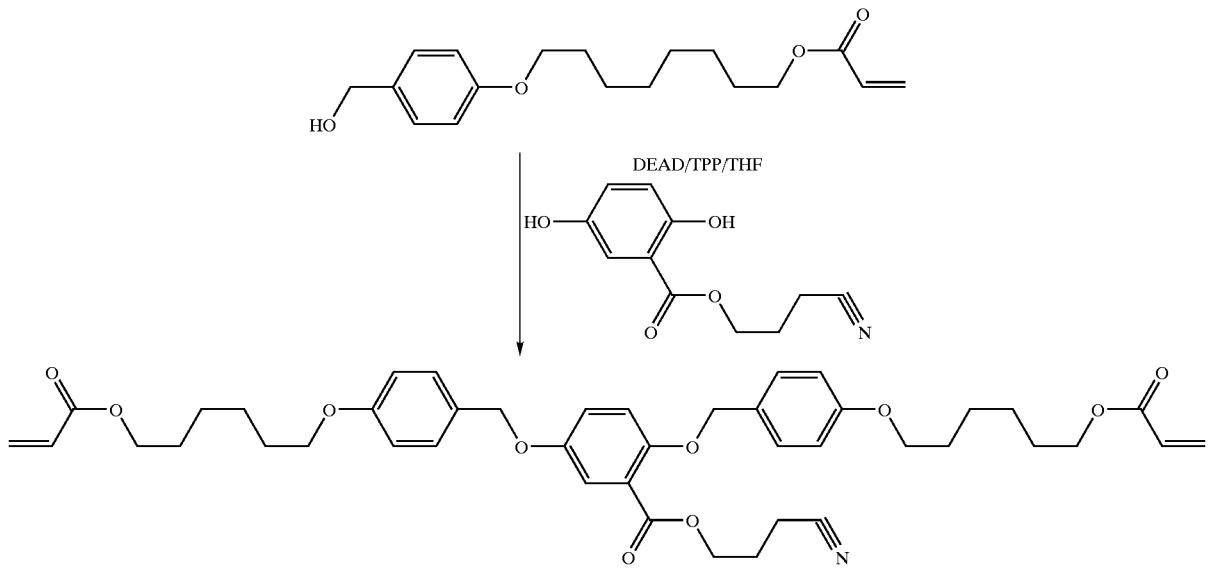

Suitable starting materials used in the preparation of the compounds of the present invention include, amongst others, phenyl and biphenyl carboxylic acid compounds as well as 1,4-cyclohexanedione. The compounds of the invention are preferably prepared by forming a ring that includes a lateral group prior to linking the mesogenic residues. Alternatively, the compounds may be prepared by forming a ring that includes a polymerisable mesogenic residue prior to linking the lateral group. A second aspect of the invention therefore provides a method of preparation of a compound of formula (I), the method comprising formning a ring that includes a lateral group and subsequently linking the mesogenic residue thereto. The mesogenic residues $G^1$ and $G^2$ are preferably attached simultaneously. As indicated above, it is especially preferred that the mesogenic residues $G^1$ and $G^2$ are identical.

It will be appreciated that the compounds of the invention may be used in the preparation of liquid crystalline mixtures. Such mixtures may be prepared by admixing a compound of formula (II) with one or more additional components. An organic solvent may also be used in the preparation of these mixtures. A third aspect of the invention therefore provides a liquid crystalline mixture comprising a compound of formula (I) and one or more additional components. The one or more additional components present in the liquid crystalline mixture may be further compounds of formula (I), other mesogenic compounds, compounds that are compatible with a mesogenic molecular architecture or chiral dopants for the introduction of helical pitch. The LCP mixture may also include a suitable organic solvent. Examples of solvents that may be used in the preparation of such liquid crystalline mixtures include anisole, caprolactone, cyclohexanone, methyl ethyl ketone, methyl propyl ketone and the like.

Examples of additional components that may be used in the preparation of liquid crystalline LCP mixtures according to the third aspect of the invention include those compounds represented by formulae III to X.

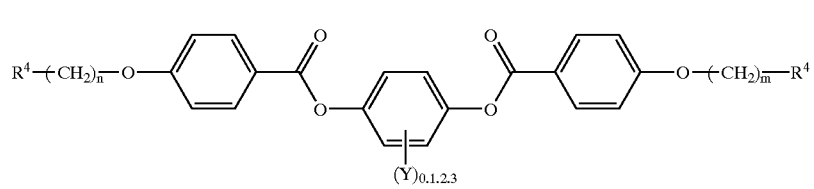

III

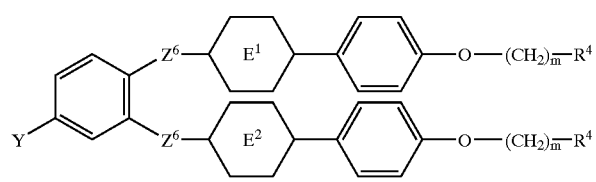

IV

-continued
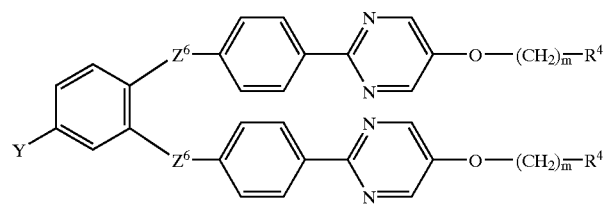
V
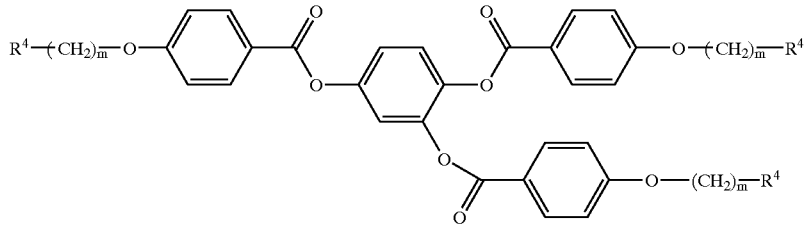
VI
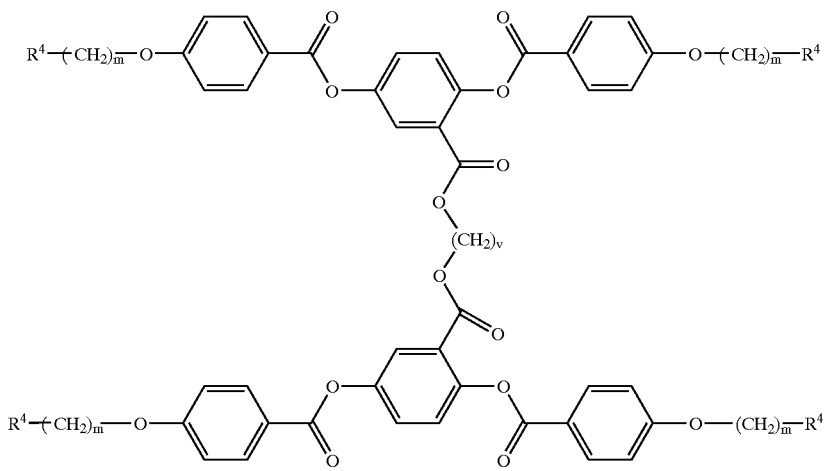
VII
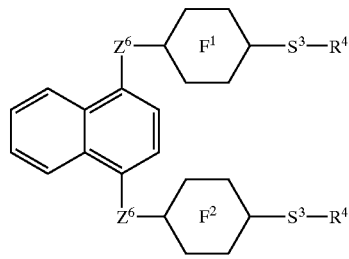
VIII
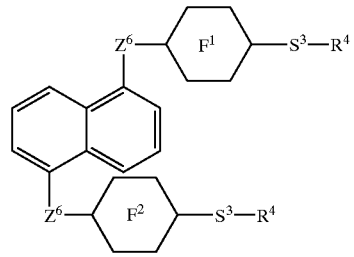
IX
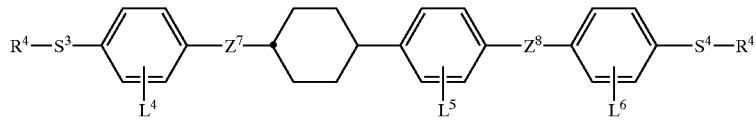
X in which R⁴ is selected from the group consisting $CH_2=CH-O-$, $CH_2=CH-COO-$, $CH_2=C(CH_3)-COO-$, $CH_2=C(Cl)-COO-$ and

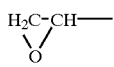

S³, S⁴ independently represent $-(CH_2)_n-$ or $-O(CH_2)_n-$;

E¹, E² are independently selected from the group consisting 1,4-phenylene trans-1,4-cyclohexylene, pyridine-2,5-diyl, pyrimidine-2,5-diyl and trans 1,4-cyclohexylene-1,4-phenylene;

F¹, F² are independently selected from the group consisting 1,4-phenylene, and 2- or 3-fluoro-1,4-phenylene;

L⁴, L⁵, L⁶ are independently selected from the group consisting OH, $C_1-C_{20}$-alkyl, $C_1-C_{20}$-alkenyl, $C_1-C_{20}$-alkoxy, $C_1-C_{20}$-alkoxy-carbonyl, formyl, $C_1-C_{20}$-alkylcarbonyl, $C_1-C_{20}$-alkylcarbonyloxy, halogen, cyano and nitro;

Z⁶ is selected from the group consisting $-COO-$, $-OOC-$, $-OCH_2-$, $-CH_2O-$, $-O(CH_2)_3-$, $-OOC(CH_2)_2-$ and $-COO(CH_2)_3-$;

Z⁷ is selected from the group consisting a single bond, $-CH_2CH_2-$, $-CH_2O-$, $-OCH_2-$, $-COO-$, $-OOC-$, $-(CH_2)_4-$, $-O(CH_2)_3-$, $(CH_2)_3O-$ and $-C\equiv C-$;

Z⁸ is selected from the group consisting a single bond, $-CH_2CH_2-$, $-CH_2O-$, $-OCH_2-$, $-COO-$, $-OOC-$, and $-C\equiv C-$;

Y is independently selected from the group consisting hydroxy, $C_1-C_{20}$-alkyl, $C_1-C_{20}$-alkenyl, $C_1-C_{20}$-alkoxy, $C_1-C_{20}$-alkoxycarbonyl, formyl-, $C_1-C_{20}$-alkylcarbonyl, $C_1-C_{20}$-alkylcarbonyloxy, fluoro, chloro, bromo, cyano and nitro;

m is an integer having a value of from 2 to 20; and v is an integer having a value of from 2 to 12.

The compounds of the invention may also be used in the formation of a LCP layer by casting a LCP compound according to the first aspect of the invention or a mixture according to the third aspect of the invention onto a substrate. A fourth aspect of the invention therefore provides a method forming a LCP network comprising forming a LCP layer including a compound of formula (I) and cross-linking the layer. Liquid crystalline mixtures according to the third aspect of the invention may also be used in the manufacture of LCP networks in a similar way.

The invention also includes, in a fifth aspect of the invention, a cross-linked LCP network comprising a compound of formula (I) in a cross-linked form. Cross-linked LCP networks comprising a mixture according to the third aspect of the invention in cross-linked form may also be included in this aspect of the invention.

A sixth aspect of the invention provides the use of a compound of formula (I) in the preparation of an optical or an electro-optical device. The use, in the preparation of an optical or electro-optical device, of liquid crystalline mixtures according to the third aspect of the invention is also included in this aspect of the invention.

An seventh aspect of the invention provides an optical or an electro-optical device comprising a compound of formula (I) in a cross-linked state. An optical or electro-optical device comprising a LCP liquid crystalline mixture in a cross-linked state according to the third aspect of the invention is also included in this aspect of the invention.

The invention will now be described with reference to the following non-limiting examples. These examples are provided by way of illustration only. Variations on these examples falling within the scope of the invention will be apparent to a skilled person.

EXAMPLES

Example 1

Synthesis of 3-cyanopropyl 2,5-dihydroxybenzoate

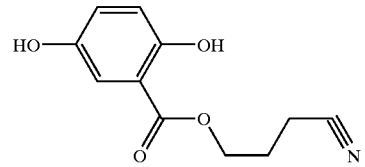

A mixture of 2,5-dihydroxybenzoic acid (4.6 g; 30 mmol), 1,8-diazabicyclo[5.4.0]undec-7-ene (5.0 g; 33 mmol), 4-bromobutyronitrile (4.9 g; 33 mmol) and acetonitrile (70 ml) was heated under reflux overnight. The reaction mixture was added to water (500 ml) and extracted with ethyl acetate (3×100 ml). The combined organic layers were washed with 1N-hydrochloric acid (150 ml) and water (2×150 ml), dried over magnesium sulphate and filtered. The organic solvent was then removed in vacuo. The residue (6.2 g) was recrystallised from ethyl acetate/hexane to yield 5.2 g (78%) of the desired 3-cyanopropyl 2,5-dihydroxybenzoate.

Synthesis of 2,5-bis-[4-(6-acryloyloxy-hexyloxy) benzoyloxy]benzoic acid 3-cyanopropyl ester

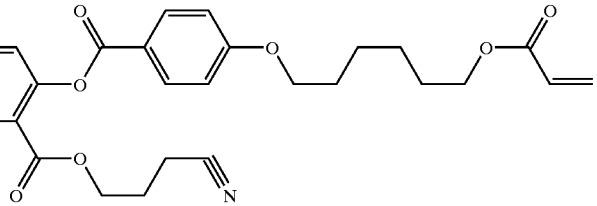

A solution of N-(3-dimethylaminopropyl)-N'-ethylcarbodiimide hydrochloride (6.5 g; 39.9 mmol) in dichloromethane (100 ml) was added slowly to a solution of 3-cyanopropyl 2,5-dihydroxybenzoate (9.9 g; 33.9 mmol), 4-(6-acryloylhexyloxy)-benzoic acid (5.7; 19.5 mmol) and 4-dimethylaminopyridine (0.8 g; 6.7 mmol) in dichloromethane (60 ml) at 0° C. The mixture was stirred at room temperature overnight. It was then added to water (300 ml) and extracted with dichloromethane (3×100 ml). The combined organic layers were washed with water (2×130 ml), dried over magnesium sulphate and filtered. The organic solvent was then removed in vacuo. The residue (14.0 g) was purified by column flash chromatography on silica gel using toluene/ethyl acetate (85:15) as eluent, to yield 6.3 g (60.6%) of 2,5-bis-[4-(6-acryloyl-oxy) hexyloxybenzoyloxy]benzoic acid 3-cyanopropyl ester. Mp=42° C.; Clp (N–I)=63.7° C. This compound may be supercooled.

The following compounds were prepared in a similar way.

2,5-bis-[4-(6-acryloyloxyhexyloxy)benzoyloxy] benzoic acid 2-cyanoethyl ester

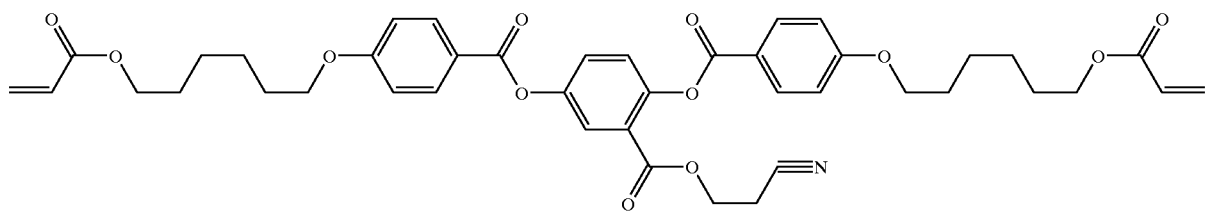

Mp=46.5° C.; Clp (N–I)=61° C.
The compound may be supercooled.

2,5-bis-[4-(6-(2-methacryloyloxy)hexyloxy) benzoyloxy]benzoic acid 3-cyanopropyl ester

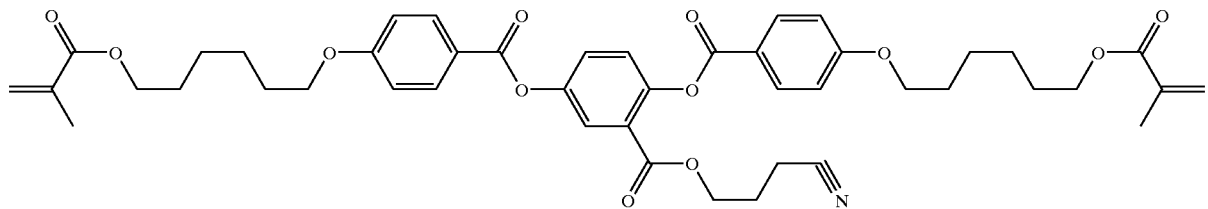

Mp=10° C.; Clp (N–I)=41.4° C.

2,5-bis-[4-(6-acryloyloxyhexyloxy)benzoyloxy] benzoic acid 4-cyanobutyl ester

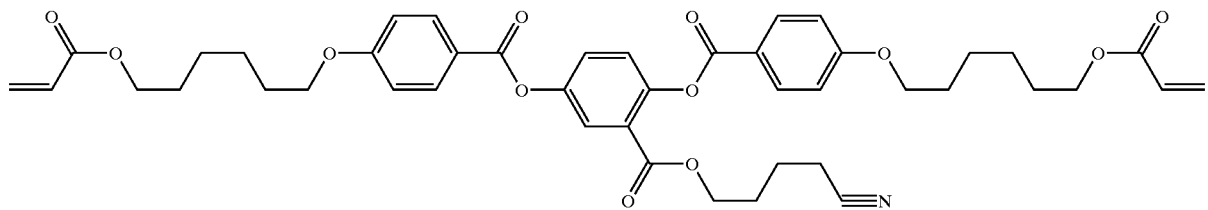

Mp=79° C.; Clp (N–I) 56° C.

2,5-bis-[4-(6-acryloyloxyhexyloxy)benzoyloxy]
benzoic acid 5-cyanopentyl ester

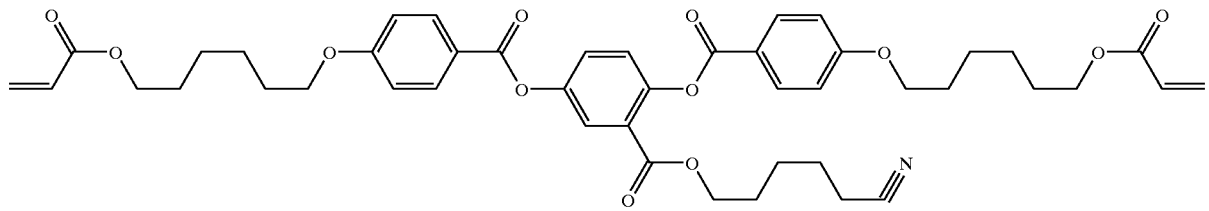

Mp=85° C.; Clp (N–I) 63.1° C.

2,5-bis-[4-(6-acryloyloxyhexyloxy)benzoyloxy]
benzoic acid 6-cyanohexyl ester

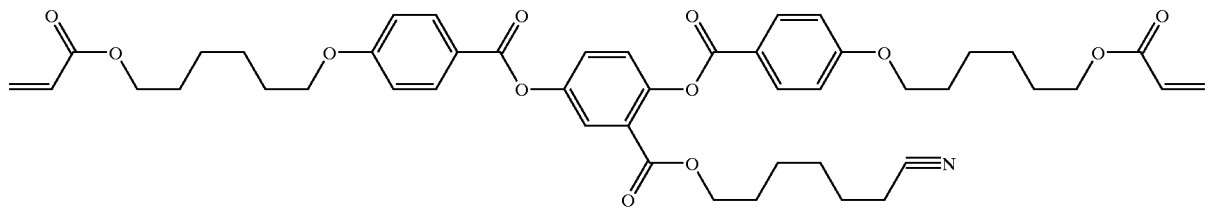

Mp=57° C.; Clp (N–I)=58.2° C.
The compound may be supercooled.

2,5-bis-[4-(5-acryloyloxypentyloxy)benzoyloxy]
benzoic acid 3-cyanopropyl ester

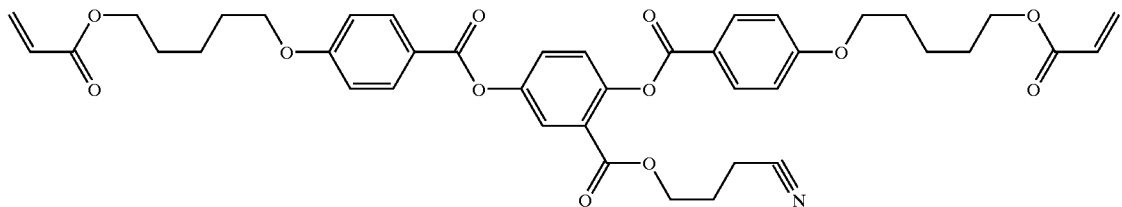

Mp=97° C.; Clp (N–I)=72.2° C.
The compound may be supercooled.

2,5-bis-[4-(8-acryloyloxyoctyloxy)benzoyloxy]
benzoic acid 3-cyanopropyl ester

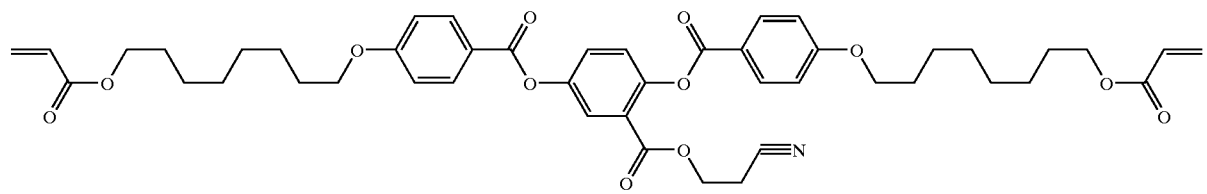

Mp 63.5° C.; Clp; (N–I)=66° C.
The compound may be supercooled.

2,5-bis-[4-(6-acryloyloxyhexyloxy)benzoyloxy]
benzoic acid 4-methoxybutyl ester

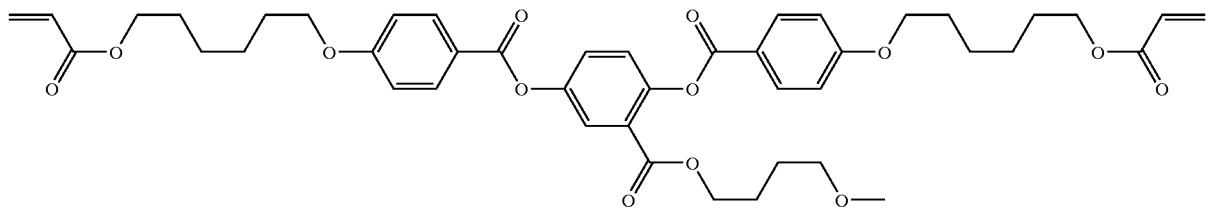

Clp (N–I)=59° C.
The compound may be supercooled.

[[3-(ethoxycarbonyl)propoxy]carbonyl]-p-phenylene
bis[p-[6-(acryloyloxy)hexyl oxy]benzoate      20

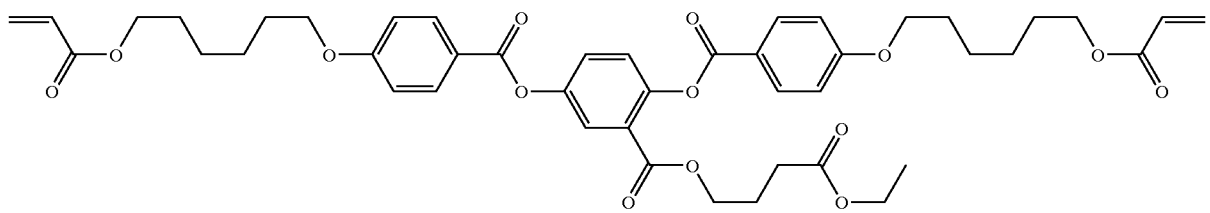

[[(6-chlorohexyl)oxy]carbonyl]-p-phenylene bis[p-
[6-(acryloyloxy)hexyloxy]-benzoate]      35

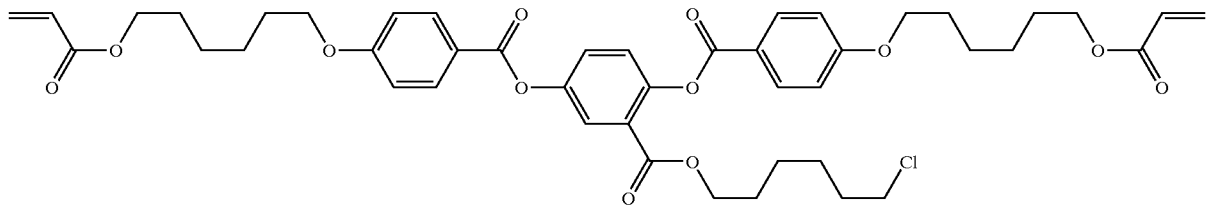

Mp=44° C.; Clp (N–I)=62.6° C.

[(4-phenoxybutoxy)carbonyl]-p-phenylene bis [p-[6-
(acryloyloxy)hexyloxy]-benzoate]

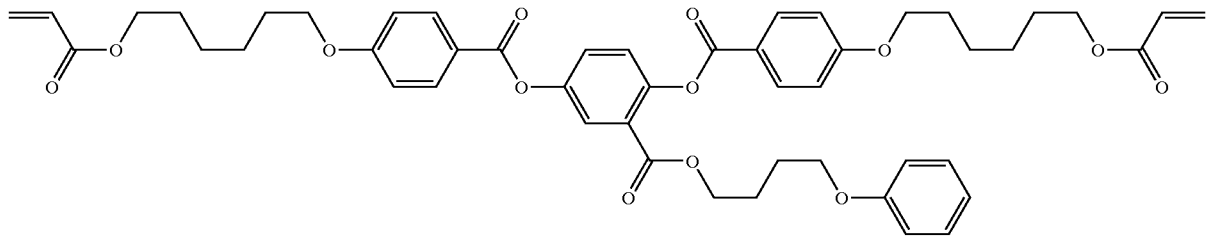

[(4,4,4-trifluorobutoxy)carbonyl]-p-phenylene bis[p-[6-(acryloyloxy)hexyloxy]-benzoate]

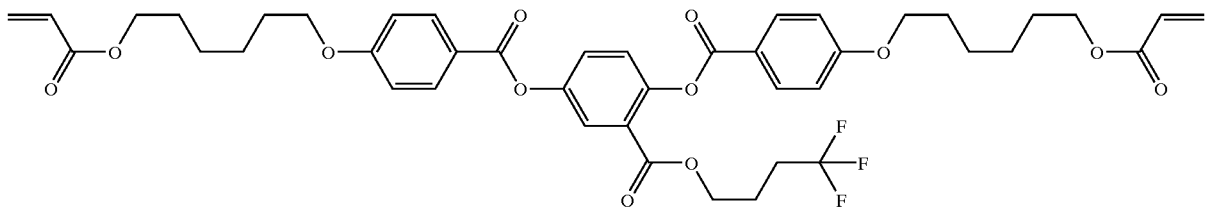

Mp=69.7° C.; Clp (N–I)=55 1° C.
The compound may be supercooled.

[trans-4-butylcyclohexyl)methoxycarbonyl]-p-phenylene bis[p-([6-(acryloyloxy)hexyl]oxy]-benzoate

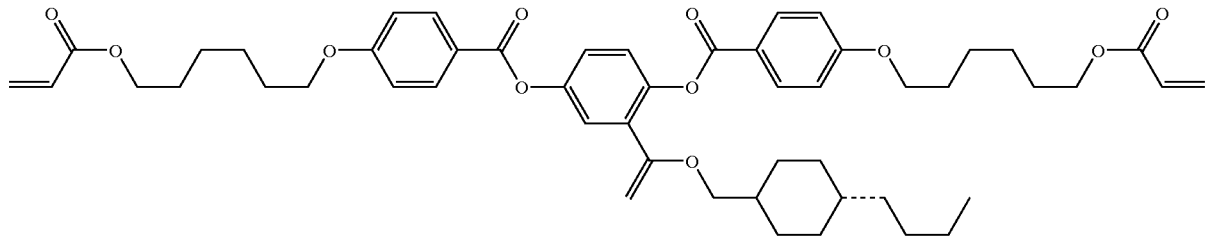

Mp=66° C.; Clp (N–I)=59.8° C. The compound may be supercooled

Example 2

Synthesis of 8-chlorooctyl 2-furancarboxylate

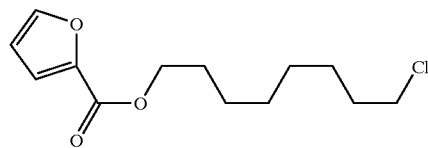

A solution of 2-furoyl chloride (6.5 g; 50 mmol) was added dropwise at 0° C. to a solution of 8-chloro-1-octanol (6.6 g; 40 mmol) and pyridine (20 g; 253 mmol) and stirred at room temperature for 2 h. The resulting mixture was added to a mixture of 1N-hydrochloric acid and ice (200 ml) and extracted with ethyl acetate (3×80 ml). The combined organic layers were washed with saturated sodium chloride solution (2×80 ml), dried over magnesium sulphate and filtered. The organic solvent was removed in vacuo to give 8-chlorooctyl-2-furancarboxylate (9.7 g) (94%) as an oil.

Synthesis of octamethylene 2,5-dihydroxybenzoate 2-furoate

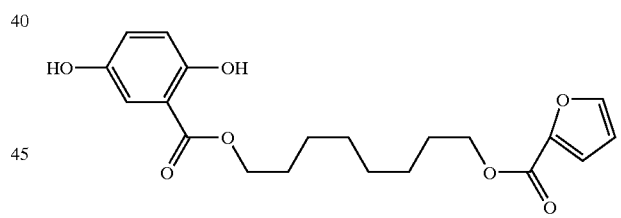

A mixture of 2,5-dihydroxybenzoic acid (5.8 g; 37 mmol), 1,8-diazabicyclo[5.4.0]undec-7-ene (5.7 g; 37 mmol), 8-chlorooctyl-2-furancarboxylate (9.7 g; 37 mmol), potassium iodide (7.8 g; 47 mmol) and acetonitrile (150 ml) was heated, under reflux for 44 h. The cooled reaction mixture was added to water (600 ml) and extracted with ethyl acetate (3×150 ml). The combined organic layers were washed with 1N-hydrochloric acid (150 ml) and water (2×150 ml), dried over magnesium sulphate and filtered. The solvent was then removed in vacuo. Recrystallisation of the residue (12.3 g) from ethyl acetate/hexane gave 9.5 g (68%) of octamethylene-2,5-dihydroxybenzoate-2-furoate.

Synthesis of furan-2-carboxylic acid 8-{2,5-bis-[4-(6-acryloyloxyhexyloxy) benzoyloxy] benzoyloxy}octyl ester

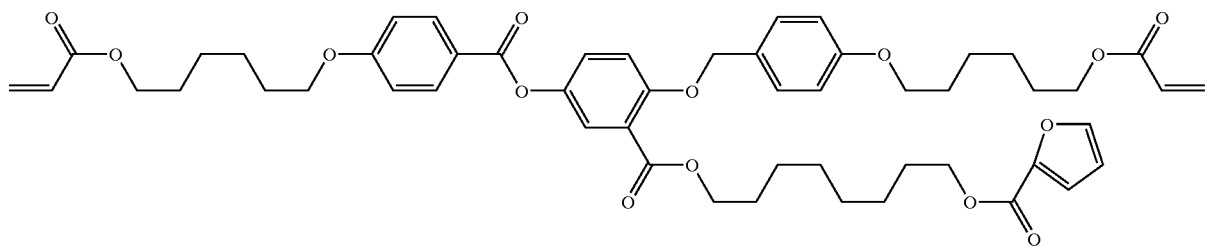

A solution of N-(3-Dimethylaminopropyl)-N'-ethylcarbodiimide hydrochloride (8.9 g: 46.5 mmol) in dichloromethane (140 ml) was slowly added to a solution of octamethylene-2,5-dihydroxybenzoate-2-furoate (7.0 g; 18.6 mmol), 4-(6-acryloylhexyloxy)benzoic acid (13.6 g; 46.5 mmol) and 4-dimethylaminopyridine (1.1 g; 9.3 mmol) in dichloromethane (130 ml) at 0° C. The mixture was stirred overnight at room temperature. The resulting solution was then added to water (600 ml) and extracted with dichloromethane (3×250 ml). The combined organic layers were washed with water (2×200 ml), dried over magnesium sulphate and filtered. The solvent was removed in vacuo.

The residue (21.0 g) was purified by column flash chromatography on silica gel using toluene/ethyl acetate (93:7) as eluent, to give 8.3 g (48,2%) of furan-2-carboxylic acid 8-{2,5-bis-[4-(6-acryloyloxyhexyloxy)benzoyloxy]-benzoyloxy}octyl ester Mp=36° C.; Clp (N–I)=41.2° C. The compound may be supercooled.

The following compounds were prepared in a similar manner.

(RS)-tetrahydrofuran-2-carboxylic acid 8-{2,5-bis-[4-(6-acryloyloxyhexyloxy) benzoyloxy] benzoyloxy}octyl ester

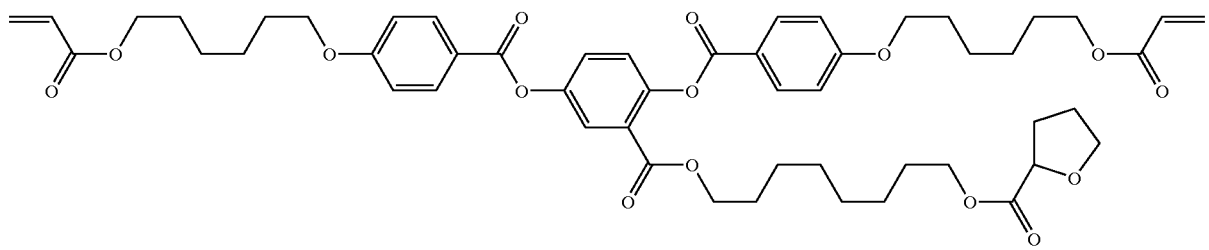

Clp (N–I)=27° C.

Furan-2-carboxylic acid 11-{2,5-bis-[4-(6-acryloyloxyhexyloxy)benzoyloxy] benzoyloxy}undecyl ester

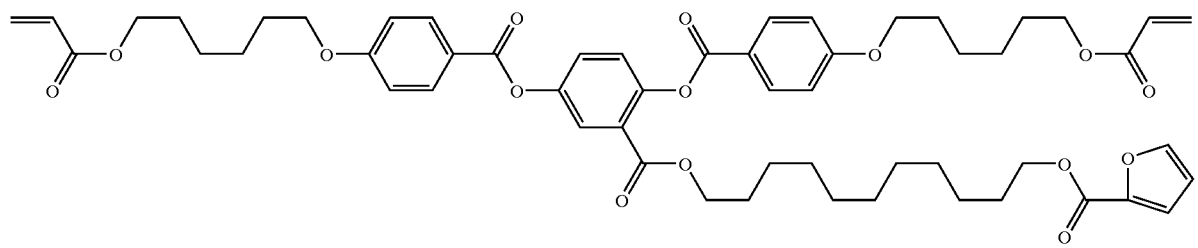

Mp=43.9° C.; Clp (N–I)=45.8° C.
The compound may be supercooled.

Furan-2-carboxylic acid 4-{2,5-bis-[4-(6-acryloyloxyhexyloxy)benzoyloxy]benzoyloxy}butyl ester

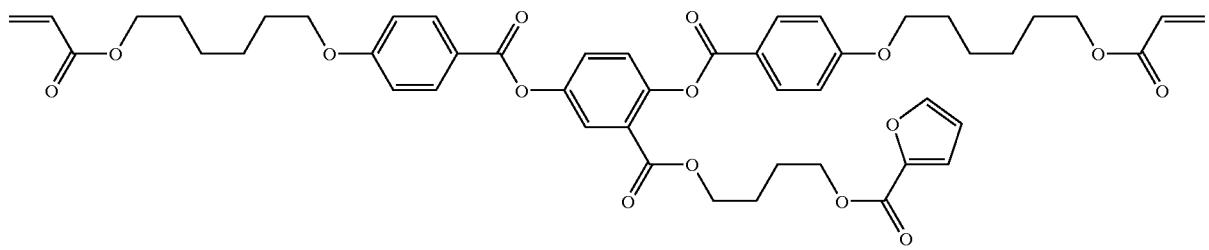

Clp (N–I)=40.7° C.

The compound may be supercooled.

Example 3

Synthesis of p-[8-chlorooctyl)oxy]benzonitrile

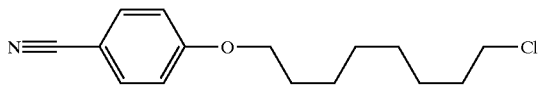

A solution of diethyl azodicarboxylate (7.3 g; 42 mmol) and tetrahydrofuran (15 ml) was added dropwise at 0° C. to a solution of 4-hydroxybenzonitrile (4.2 g; 35 mmol), 8-chloro-1-octanol (6.9 g; 42 mmol), triphenylphosphine (11.0 g; 42 mmol) and tetrahydrofuran (70 ml) and stirred at room temperature overnight. The reaction mixture was added to water (200 ml) and extracted with ethyl acetate (3×100 ml), dried over magnesium sulphate and filtered. The solvent was then removed in vacuo. The residue was purified by column flash chromatography on silica gel using toluene/ethyl acetate (97:3) as eluent, to give 8.8 g (94%) of p-[(8-chlorooctyl)oxy]benzonitrile.

Synthesis of 8-(p-cyanophenoxy)octyl 2,5-dihydroxybenzoate

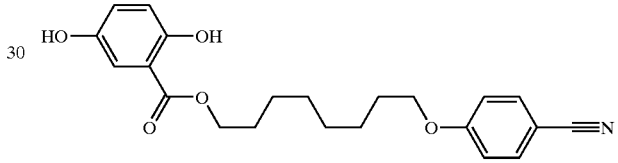

A mixture of 2,5-dihydroxybenzoic acid (4.2 g; 27.5 mmol), 1.8-diazabicyclo[5.4.0]undec-7-ene (4.2 g; 27.5 mmol), potassium iodide (41.0 g; 247 mmol), p-[(8-chlorooctyl)oxy]benzonitrile (6.6 g; 25 mmol) and acetonitrile (100 ml) was heated under reflux for 72 h. The reaction mixture was cooled, poured into water (500 ml) and extracted with ethyl acetate (3×150 ml). The combined organic layers were washed with 1N-hydrochloric acid (150 ml) and water (2×150 ml), dried over magnesium sulphate and filtered. The solvent was removed in vacuo. The residue was purified by column flash chromatography on silica gel using a toluene/ethyl acetate 80:20 as eluent to give 8.0 g (84%) of 8-(p-cyanophenoxy)octyl 2,5-dihydroxybenzoate.

Synthesis of 2,5-bis-[4-(6-acryloyloxyhexyloxy) benzoloxy]benzoic acid 8-(4-cyano-phenoxy)octyl ester

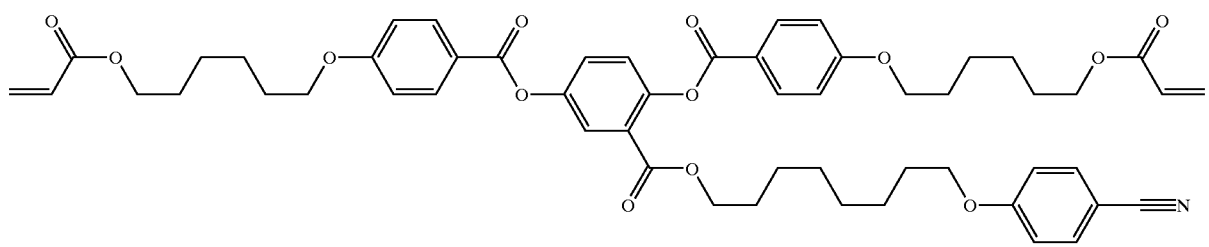

A solution of N-(3-dimethylaminopropyl)-N'-ethylcarbodiimide hydrochloride (3.7 g; 19.5 mmol) in dichloromethane (60 ml) was added slowly to a solution of 8-(p-cyanophenoxy)octyl-2,5-dihydroxybenzoate (3 g; 7.8 mmol), 4-(acryloylhexyloxy)benzoic acid (5.7 g; 19.5 mmol) and 4-dimethylaminopyridine (0.5 g; 3.9 mmol) in dichloromethane (80 ml) at 0° C. The mixture was stirred overnight at room temperature. The resulting mixture was added to water (350 ml) and extracted with dichloromethane (3×100 ml). The combined organic layers were washed with water (2×100 ml), dried over magnesium sulphate and filtered. The organic solvent was removed in vacuo. The residue (9.0 g) was purified by flash chromatography using a silica gel column and toluene/ethyl acetate (98:2) as eluent, to give 4.6 g (63%) of 2,5-bis-[4-(6-acryloyloxyhexyloxy)benzoyloxy]benzoic acid 8-(4-cyanophenoxy)octyl ester. Mp=54.5° C.; Clp (N–I)=78.4° C.; ($S_A$-N)=43.5° C. The compound may be supercooled.

Example 4

Synthesis of 4-hydroxy-4'-methoxy-3-biphenylcarboxylic acid

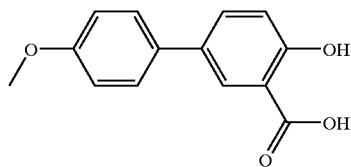

Palladium(II)acetate (55 mg; 0.23 mmol) was added under argon to a mixture of 5-bromosalicylic acid (5.4 g; 22.4 mmol), sodium carbonate (7.2 g; 68.1 mmol) and 4-methoxyboronic acid (3.8 g; 25 mmol) in water (125 ml). The reaction mixture was stirred at room temperature for 1 h. The resulting slurry was dissolved in hot water (1300 ml) and filtered to give a filtrate and a precipitate. The filtrate was acidified with hydrochloric acid. The precipitate was washed with water and dried in vacuo to give 5.3 g (95%) of 4-hydroxy-4'-methoxy-3-biphenylcarboxylic acid.

Synthesis of 4,4'-dihydroxy-3-biphenylcarboxylic acid

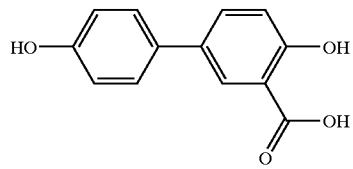

A solution of 4-hydroxy-4'-methoxy-3-biphenylcarboxylic acid (5.3 g; 21.6 mmol), tetrabutylphosphonium bromide (0.8 g; 2.3 mmol), acetic acid (35 ml) and hydrobromic acid (35 ml of a 48% solution) was heated at reflux for 6 h. The reaction mixture was cooled and poured into water (400 ml). The resulting precipitate was isolated and recrystallised from ethyl acetate to give 2.4 g (47%) of 4,4'-dihydroxy-3-biphenyl-carboxylic acid.

Synthesis of 3-cyanopropyl-4,4'-dihydroxy-3-biphenylcarboxylate

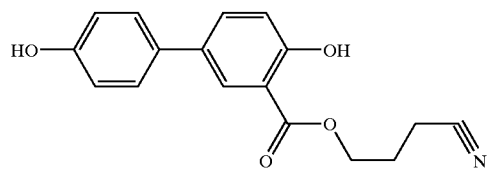

A mixture of 4,4'-dihydroxy-3-biphenylcarboxylic acid (2.3 g; 10 mmol), 1,8-diaza-bicyclo[5.4.0]undec-7-ene (1.7 g; 11.2 mmol), 4-bromobutyronitrile (1.7 g; 11.2 mmol) and N,N-dimethylformamide (40 ml) was heated at 75° C. for 4 h. The reaction mixture was cooled, poured into water (300 ml) and extracted with ethyl acetate (3×100 ml). The combined organic layers were washed with 1N-hydrochloric acid (150 ml) and with water (2×100 ml), dried over magnesium sulphate and filtered. The organic solvent was removed in vacuo. The residue (3.0 g) was purified by flash chromatography using a silica gel column and toluene/ethyl acetate (97:3) as eluent to give 2.1 g (70%) of 3-cyanopropyl-4,4'-dihydroxy-3-biphenylcarboxylate.

Synthesis of 3-[(3-cyanopropoxy)carbonyl]-4,4'-biphenylene bis[p-[6-(acryloyloxy)hexyloxy] benzoate]

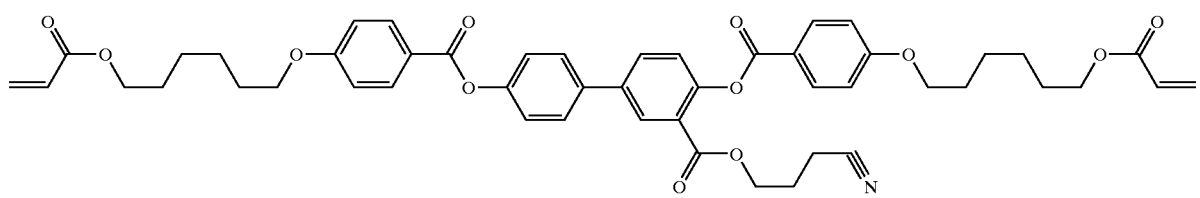

A solution of N-(3-dimethylaminopropyl)-N'-ethylcarbodiimide hydrochloride (2.9 g; 15.4 mmol) in dichloromethane (50 ml) was slowly added to a solution of 3-cyanopropyl-4,4'-dihydroxy-3-biphenylcarboxylate (2.1 g; 7.1 mmol), 4-(6-acryloylhexyloxy)benzoic acid (4.5 g; 15.4 mmol) and 4-dimethylaminopyridine (0.5 g; 3.9 mmol) in dichloromethane (80 ml) at 0° C. The mixture was stirred at room temperature overnight. The resulting mixture was added to water (300 ml) and extracted with dichloromethane

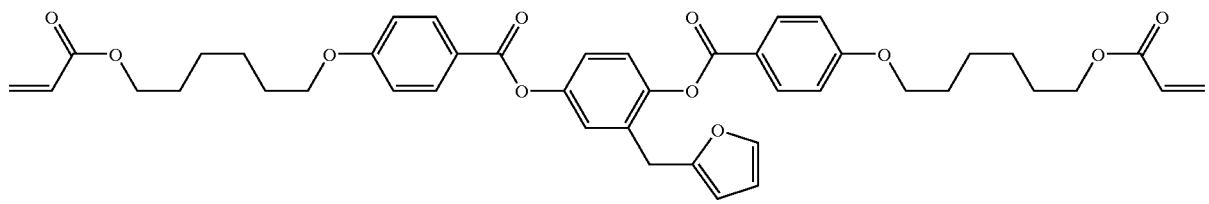

(3×100 ml). The combined organic layers were washed with water (2×100 ml), dried over magnesium sulphate and filtered. The organic solvent was removed in vacuo. The residue (6.3 g) was purified by flash chromatography using a silica gel column and toluene/ethyl acetate (90:10) as eluent, to yield 1.3 g (20%) of 3-[(3-cyanopropoxy)carbonyl]4,4'-biphenylene bis[p-[6-(acryloyloxy)hexyloxy] benzoate]. Mp=85.5° C.; Clp (N–I)=154.5° C. The compound may be supercooled.

The following compound was prepared in a similar way:

3-[(3-cyanopropoxy)carbonyl]-4-(trans-4-cyclohexyl)-phenyl bis[p-([6-(acryloyloxy)hexyl]oxy)benzoate]

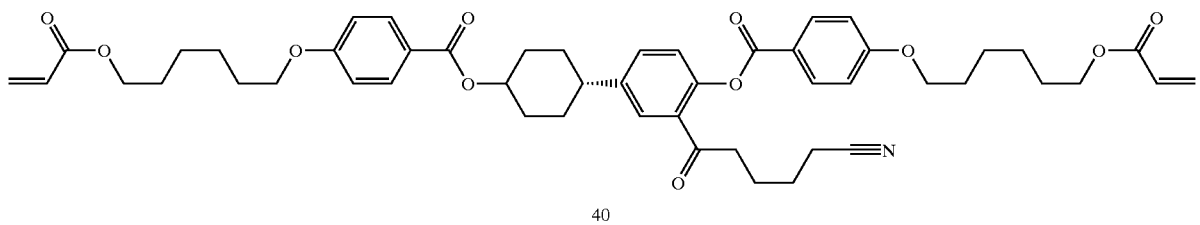

Mp=98° C.; Clp (N–I)=140° C.

Example 5

Synthesis of 2-furfurylhydroquinone

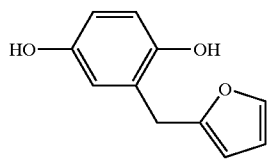

A mixture of 1,4-cyclohexanedione (5.6 g; 50 mmol), furan-2-carbaldehyde (4.8 g; 50 mmol) and anhydrous lithium chloride (2.1 g; 50 mmol) in 1,3-dimethyl-2-imidazolidinone (20 ml) was heated with stirring over an a oil bath at atmospheric pressure. The temperature of the bath was maintained at 165° C. for 1 h. The cooled reaction mixture was poured into water (300 ml) and extracted with ethyl acetate (2×150 ml). The combined organic layers were washed with water (2×100 ml), dried over magnesium sulphate and filtered. The organic solvent was removed in vacuo. The residue (9.4 g) was purified by flash chromatography using a silica gel column and toluene/ethyl acetate (90:10) as eluent, to give 6.7 g (70%) of 3-furfurylhydroquinone.

Synthesis of 4-(6-acryloyloxyhexyloxy)benzoic acid 4-[4-(6-acryloyloxyhexyloxy)benzoyloxy]3,3-furan-2-ylmethylphenyl ester A solution of N-(3-dimethylaminopropyl)-N'-ethylcarbodiimide hydrochloride (8.8 g; 46 mmol) in dichloromethane (160 ml) was added slowly to a solution of 2-furfurylhydroquinone (3.5 g; 18.4 mmol), 4-(6-acryloylhexyloxy)benzoic acid (13.4 g; 46 mmol) and 4-dimethylaminopyridine (0.5 g; 3.9 mmol) in dichloromethane (50 ml) at 0° C. The reaction mixture was stirred at room temperature overnight, added to water (350 ml) and extracted with dichloromethane (3×100 ml). The combined organic layers were washed with water (2×100 ml) dried over magnesium sulphate and filtered. The organic solvent was removed in vacuo. The residue (18.6 g) was purified by flash chromatography using a silica gel column and toluene/ethyl acetate (95:5) as eluent and recrystallised from ethyl acetate/hexane to give 6.4 g (47%) of 4-(6-acryloyloxyhexyloxy)benzoic acid 4-[4-(6-acryloyloxyhexyloxy)benzoyloxy]-3-furan-2-yl methylphenyl ester. Mp=65° C. Clp (N–I)=51° C. The compound may be supercooled.

Example 6

Synthesis of [[(3-cyanopropoxy)carbonyl]-p-phenylene]bis[oxymethylene-p-phenyleneoxyhexamethylene]diacrylate

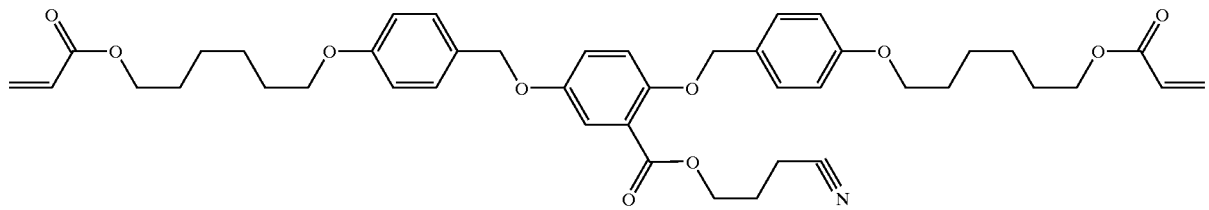

A solution of diethyl azodicarboxylate (4.2 g; 24 mmol) and tetrahydrofuran (20 ml) was added dropwise at 0° C., to a solution of triphenylphosphine (6.4 g; 24 mmol) into tetrahydrofuran (40 ml), the salt mixture was stirred for 2 h at 0° C. After the salt mixture was added slowly at 0° C. to a solution of 6-[(α-hydroxy-p-tolyl)oxy]hexyl acrylate (3.1 g; 10 mmol), 3-cyanopropyl-2,5-dihydroxybenzoate (2.2; 10 mmol) and tetrahydrofuran (60 ml), stirred at room temperature overnight. The reaction mixture was added to water (400 ml) and extracted with ethyl acetate (3×200 ml). The combined organic layers were washed with water (2×200 ml), dried over magnesium sulphate, filtered and then evaporated down under reduced pressure. The residue (16.0 g) was purified by column flash chromatography on silica gel using a 95:5 toluene/ethyl acetate mixture as eluent. to yield 2. 3 g (31%) of the desired ether.

The following compound may be synthesised using a similar method:

[[(3-cyanopropoxy)carbonyl]-p-phenylene]bis[oxymethylene(trans-1,4-cyclohexylene)oxyhexamethylene]diacrylate

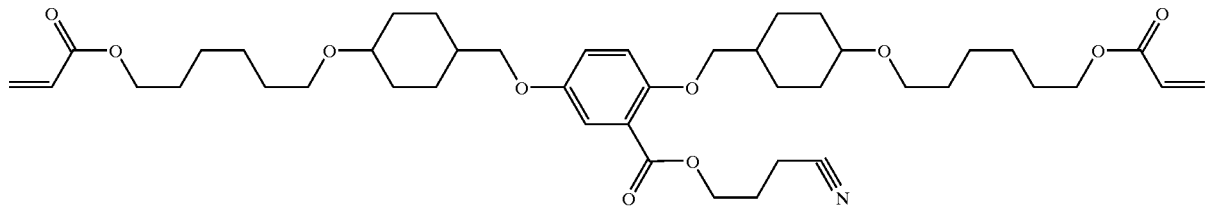

Example 7

Preparation of nematic LCP Films (i) A mixture of the following components in anisole was prepared:

70 wt % of

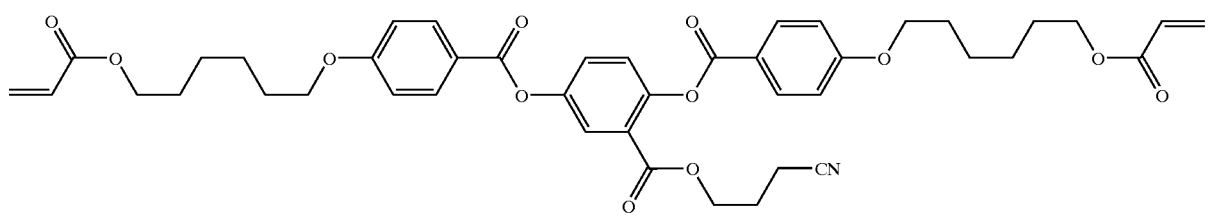

30 wt % of

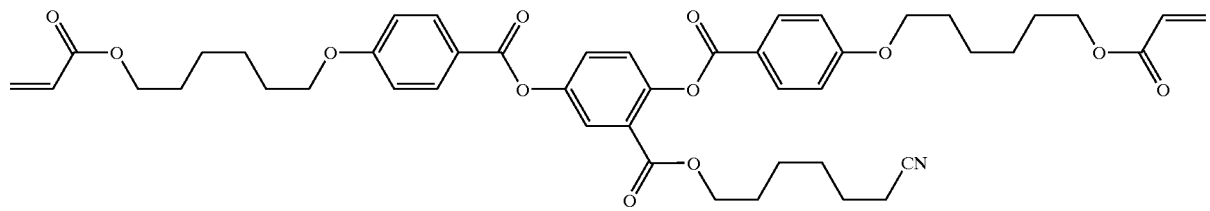

1000 ppm of a Tinuvin 123 stabiliser and 500 ppm of a 2,6-di-(t-butyl)-4-hydroxytoluene (BHT) inhibitor were added to this mixture. 500 ppm of an Irgacure 369 polymerisation initiator (commercially available from Ciba Geigy, Basle, Switzerland) was added. The mixture was stirred at room temperature and then spincoated on a glass plate having an orientation layer to form an LCP film of approximately 800 nm in thickness. This film was dried at 50° C. for 1 or 2 minutes and photopolymerised by irradiation with UV light for approximately 5 minutes at room temperature in a $N_2$ atmosphere using a mercury lamp.

The film exhibits a nematic mesophase at room temperature. In addition this film exhibits a tilt angle of about 10° relative to the plane of the substrate, as shown by ellipsometric measurements. The non-polymerised film exhibits an excellent super cooling behaviour.

(ii) A mixture of the following components in anisole was prepared according to procedure (i) above.

60 wt % of

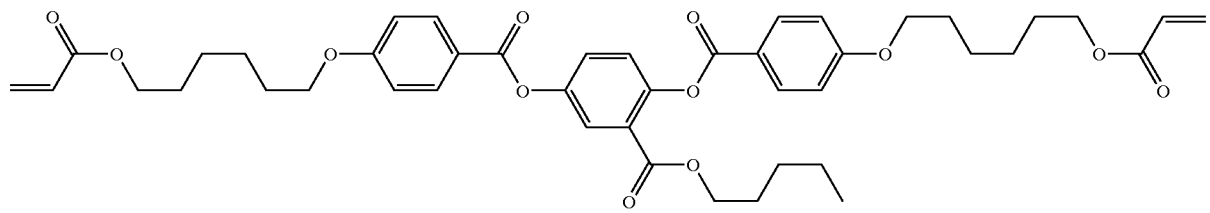

20 wt % of

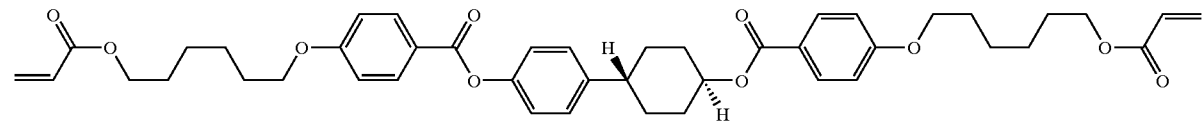

10 wt % of

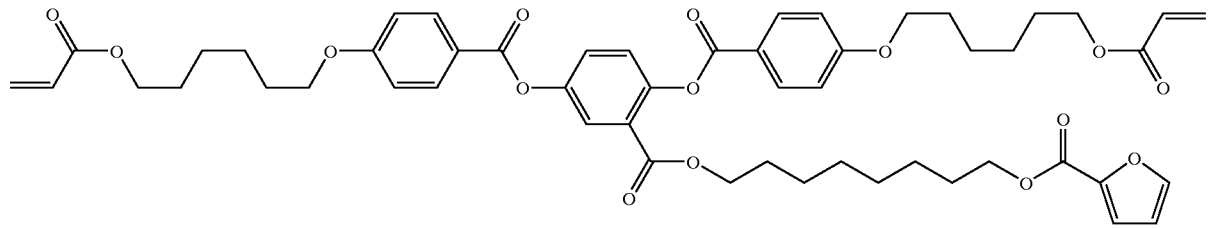

and 10 wt % of 1,4-butanediol diacrylate (Aldrich)

The nematic film formed exhibits a well oriented nematic mesophase at room temperature with a clearing point of 80° C. In addition this film exhibits a tilt angle of about 1° relative to the plane of the substrate, as shown by ellipsometric measurements.

What is claimed is:

1. A compound of formula (I)

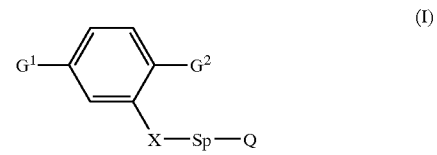

(I)

wherein $G^1$ and $G^2$ are each independently a polymerisable mesogenic residue X is —CH$_2$—, —O—, —CO—, —COO—, —OOC—, —CONR'—, —OCOO— or —OCONR';

Sp is a group of formula —(CH$_2$)$_p$— in which p is an integer ranging from 1 to 18; and in which one or two non adjacent —CH$_2$ groups are optionally replaced by —CH=CH—; or in which one or two —CH$_2$— groups may be replaced by one or two groups selected from the group consisting of —CH$_2$—, —O—, —CO—, —COO—, —OOC—, —CONR'—, —OCOO— and —OCONR'—; with the proviso that the Sp group does not contain two adjacent heteroatoms and when X is —CH$_2$—, p can also have a value of 0;

Q is —CN, —COR, —COOR, —OCOR, CONR'R, —NR'COR, —OCOOR, —OCONR'R, —NR'COOR, F, Cl, —CF$_3$, —OCF$_3$ or —OR or a cyclic group which is unsubstituted or substituted by a group selected from the group consisting of a lower alkyl, lower alkenyl, lower alkoxy, lower alkenyloxy, halogen, —CN, —COR", —COOR", —OCOR", —CONR'R", —NR'COR", —OCOOR", —OCONR'R", —NR'COOR", —CF$_3$ and —OCF$_3$; where R is hydrogen, a lower alkyl, a lower alkenyl or a cyclic group which is unsubstituted or substituted by a group selected from the group consisting of a lower alkyl, lower alkenyl, lower alkoxy, lower alkenyloxy, halogen, —CN, —COR", —COOR", —OCOR", —CONR'R", —NR'COR", —OCOOR", —OCONR'R", —NR'COOR", —CF$_3$ and —OCF$_3$;

R' is hydrogen, a lower alkyl or lower alkenyl group, and

R" is a lower alkyl or a lower alkenyl group.

2. A compound according to claim 1, in which G$^1$ and G$^2$ are the same.

3. A compound according to claim 1 in which X is —CH$_2$—, —O—, —COO— or —OOC—.

4. A compound according to claim 1 wherein said p ranges from 1 to 11.

5. A compound according claim 1 wherein no more than one —CH$_2$— moiety of the Sp group is replaced by —CH=CH—, —O—, CO—, —COO—, —OOC—, —CONR'—, —OCOO—, OCONR'.

6. A compound according claim 1 wherein Q is —CN, —COOR, —OCOR, Cl, —CF$_3$, —OCF$_3$, —OR or a cyclic group.

7. A compound according claim 1 wherein said cyclic group is selected from the group consisting of five or six membered saturated isocyclic moieties, five or six membered saturated heterocyclic moieties, five or six membered unsaturated isocyclic moieties and five or six membered unsaturated heterocyclic moieties.

8. A compound according claim 1 wherein said cyclic group is optionally substituted by a group selected from the group consisting of a lower alkyl, lower alkoxy, F, Cl, —CN, —COOR", —OCOR", —OCF$_3$, and OR", in which R" is a lower alkyl.

9. A compound according claim 1 wherein said mesogenic residues G$^1$ and G$^2$ are of formula II

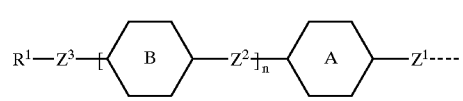

(II)

wherein

A and B are each independently 1,4-phenylene, pyridine-2,5-diyl, pyrimidine-2,5-diyl, trans-1,4-cyclohexylene or trans-1,3-dioxane-1,4-diyl; optionally substituted with a halogen, —CN, a lower alkyl, lower alkenyl, lower alkoxy or lower alkenyloxy group;

n is 1 or 0;

Z$^1$ and Z$^2$ are each independently a single bond, —COO—, —OOC—, —CH$_2$—CH$_2$—, —CH$_2$O—, —OCH$_2$—, —CH=CH—, —C≡C—, —(CH$_2$)$_4$—, or —(CH$_2$)$_3$O—;

Z$^3$ is a group of formula —(CH$_2$)$_p$X— in which one or two non adjacent —CH$_2$— groups may be optionally replaced by —CH=CH— or in which one or two —CH$_2$— groups may be replaced by one or two groups selected from the group consisting of —CH$_2$—, —O—, COO—, —OOC—, —CONR'—, —OCOO— and —OCONR'; with the proviso that the Sp group does not contain two adjacent heteroatoms and when X is —CH$_2$—, p can also have a value of 0;

wherein p is an integer ranging from 1 to 12; and

X is —CH$_2$—, —O—, CO—, —COO—, —OOC—, —CONR'—, —OCOO— or —OCONR';

R$^1$ is a polymerisable group selected from the group consisting of CH$_2$=C(Ph)-, CH$_2$=CW—COO—, CH$_2$=CH—COO-Ph-, CH$_2$=CW—CO—NH—, CH$_2$=CH—O—, CH$_2$=CH—OOC—, Ph-CH=CH—, CH$_2$=CH-Ph-, CH$_2$=CH-Ph-O—, R$^3$-Ph-CH=CH—COO—, R$^3$—OOC—CH=CH-Ph-O— and 2-W-epoxythyl in which W is H, Cl, Ph or a lower alkyl, and R$^3$ is a lower alkyl with the proviso that when R$^3$ is attached to a 1,4-phenylene group (-Ph-) it may also be hydrogen or lower alkoxy.

10. A compound according to claim 9, in which Z$^1$ and Z$^2$ are each independently a single bond, —COO—, —OOC—, —CH$_2$—CH$_2$, —CH$_2$O, —OCH$_2$—, —CH=CH— or —C≡C—.

11. A compound according to claim 9 in which R$^1$ is CH$_2$=CW—, CH$_2$=CW—COO— or CH$_2$=CH—O—.

12. An optical or electro-optical device comprising a compound according claim 1.

13. A LCP network comprising a compound according to claim 1.

14. A LCP mixture comprising a compound of formula (I)

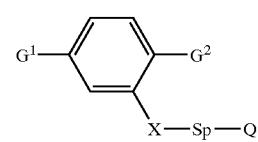

(I)

wherein

G$^1$ and G$^2$ are each independently a polymerisable mesogenic residue

X is —CH$_2$—, —O—, —CO—, —COO—, —OOC—, —CONR'—, —OCOO— or —OCONR';

Sp is a group of formula —(CH$_2$)$_p$— in which p is an integer ranging from 1 to 18 and in which one or two non adjacent —CH$_2$ groups are optionally replaced by —CH=CH—; or in which one or two —CH$_2$— groups may be replaced by one or two groups selected from the group consisting of —CH$_2$—, —O—, —CO—, —COO—, OOC—, —CONR'—, —OCOO— and —OCONR'—; with the proviso that the Sp group does not contain two adjacent heteroatoms and when X is —CH$_2$—, p can also have a value of 0;

Q is —CN, —COR, —COOR, —OCOR, CONR'R, —NR'COR, —OCOOR, —OCONR'R, —NR'COOR, F, Cl —CF$_3$, —OCF$_3$ or —OR or a cyclic group which is unsubstituted or substituted by a group selected from the group consisting of a lower alkyl, lower alkenyl, lower alkoxy, lower alkenyloxy, halogen, —CN, —COR", —COOR", —OCOR", —CONR'R", —NR'COR", —OCOOR", —OCONR'R", —NR'COOR", —CF$_3$ and —OCF$_3$;

where

R is hydrogen, a lower alkyl, a lower alkenyl or a cyclic group which is unsubstituted or substituted by a group selected from the group consisting of a lower alkyl lower alkenyl, lower alkoxy, lower alkenyloxy, halogen, —CN, —COR", —COOR", —OCOR", —CONR'R', —NR'COR", —OCOOR", —OCONR'R", —NR'COOR", —CF$_3$ and —OCF$_3$;

R' is hydrogen, a lower alkyl or lower alkenyl group, and

R" is a lower alkyl or a lower alkenyl group and one or more additional suitable components.

15. An optical or electro-optical device comprising a mixture according to claim 14 in cross-linked or polymerized form.

16. A LCP network comprising a mixture according to claim 14 in cross-linked or polymerized form.

* * * * *